United States Patent
Schmidt (10) Patent No.: US 7,021,130 B2
(45) Date of Patent: Apr. 4, 2006

(54) METHOD AND DEVICE FOR THE MEASUREMENT OF EXHAUST GAS FROM INTERNAL COMBUSTION ENGINES

(75) Inventor: Roland Schmidt, Buchholz (DE)

(73) Assignee: Pierburg Instruments GmbH, Nuess (DE)

( * ) Notice: Subject to any disclaimer, the term of this patent is extended or adjusted under 35 U.S.C. 154(b) by 16 days.

(21) Appl. No.: 10/839,943

(22) Filed: May 6, 2004

(65) Prior Publication Data

US 2004/0226354 A1   Nov. 18, 2004

(30) Foreign Application Priority Data

May 14, 2003   (EP) .................................. 03010792

(51) Int. Cl.
*G01M 19/00*   (2006.01)

(52) U.S. Cl. ..................... 73/118.1; 73/23.31; 73/23.32

(58) Field of Classification Search ............... 73/23.31, 73/23.32, 118.1, 863.03, 861.63; 701/101, 701/108, 109
See application file for complete search history.

(56) References Cited

U.S. PATENT DOCUMENTS 5,761,901 A * 6/1998 Staufenberg et al. ......... 60/274
6,405,577 B1 * 6/2002 Hanashiro et al. ......... 73/23.31
6,516,654 B1 * 2/2003 Uchihara et al. .......... 73/28.04

FOREIGN PATENT DOCUMENTS

| DE | 24 44 117 A | 3/1976 |
| DE | 40 17 472 A | 11/1991 |
| JP | 55 065133 | 5/1980 |
| WO | WO 96 01998 A | 1/1996 |

OTHER PUBLICATIONS

Patent Abstracts Of Japan, vol. 004, No. 107 (P-021), (Jul. 31, 1980).

\* cited by examiner

*Primary Examiner*—David M. Gray
*Assistant Examiner*—Freddie Kirkland, III
(74) *Attorney, Agent, or Firm*—Quarles & Brady LLP (57) ABSTRACT

A Method and device for the measurement of exhaust gas from internal combustion engines using a full-flow dilution method in which the exhaust volume flow is mixed with dilution air so that in specified test cycles, a defined total volume flow results, from which a partial sampling volume flow is extracted, on which a measurement of particulate emissions and/or gaseous components in the exhaust is conducted, and wherein a smoothed curve (II) of the exhaust flow (I) that is varied during the test cycles is determined, and the total volume flow (III) is adjusted in proportion to the variations in the measured smoothed curve of the exhaust flow.

16 Claims, 3 Drawing Sheets

PRIOR ART

METHOD AND DEVICE FOR THE MEASUREMENT OF EXHAUST GAS FROM INTERNAL COMBUSTION ENGINES

CROSS REFERENCES TO RELATED APPLICATIONS

Not Applicable.

STATEMENT REGARDING FEDERALLY SPONSORED RESEARCH

Not Applicable.

DESCRIPTION OF THE BACKGROUND ART

This invention relates to a method and a device for the measurement of exhaust gas from internal combustion engines (gasoline engines and diesel engines) according to a full-flow dilution method. The full flow dilution method is often called CVS method (Constant Volume Sampling method) because the current regulations require a CVS method which is a full flow dilution method with constant volume sampling. The method and device of the invention are suitable both for a gravimetric measurement of particulates in the exhaust gas, as well as, for a measurement of gaseous exhaust components in the emissions.

Laws and regulations in Europe and in the United States of America limit the emission of gaseous and solid/liquid pollutant components in the exhaust of gasoline and diesel engines. According to current regulations, the exhaust gas from an engine must be diluted in a CVS (Constant Volume Sampling) system.

The particulate components emitted by diesel engines are measured by a gravimetric total content measurement over the test period, i.e. a special particulates measurement filter is weighed before and after it has been charged with diluted exhaust gas from the diesel engine. The specific particulates emissions are calculated from the weight difference, taking into consideration the length of the test line (driving distance) and the work performed.

The gaseous components of the exhaust from gasoline engines are also measured in the diluted exhaust using a CVS system. In this case, the diluted exhaust gas is passed into a collecting bag, and after a test cycle has been completed, the concentration of the individual gaseous components of the exhaust in the collecting bag is determined.

In recent years, the limits for both particulates and gaseous pollutants have been drastically reduced. Consequently, the difference between the absolute amount of the measured quantity and the measurement resolution is constantly being reduced, as a result of which the accuracy of the measurement is likewise decreasing.

With regard to the applicable European provisions and the related specific requirements for measurement and instrumentation, reference is made to Directive 98/69/EC of the European Parliament and of the Council of 13 Oct. 1998 relating to measures to be taken against air pollution by emissions from motor vehicles and amending Council Directive 70/220/EEC; Directive 1999/96/EEC of the European Parliament and of the Council of 13 Dec. 1999 on the approximation of the laws of the Member States relating to measures to be taken against the emission of gaseous and particulate pollutants from compression ignition engines for use in vehicles, and the emission of gaseous pollutants from positive ignition engines fuelled with natural gas or liquefied petroleum gas for use in vehicles and amending Council Directive 88/77/EEC; Council Directive 91/441/EEC amending Directive 70/220/EEC on the approximation of the laws of the Member States relating to measures to be taken against air pollution by emissions from motor vehicles, 26 Jun. 1991; Commission Directive 2003/76/EC of 11 Aug. 2003 amending Council Directive 70/220/EEC relating to measures to be taken against air pollution by emissions from motor vehicles. Corresponding US regulations are to be found in: Code of Federal Regulations, Title 40, Part 86, Subpart B—Emission Regulations for 1977 and Later Model Year New Light-Duty Vehicles and New Light-Duty Trucks; 1999.

In a full-flow dilution system using the prescribed Constant Volume Sampling CVS, in general the total exhaust gas volume flow from a test engine is mixed with dilution air in a dilution tunnel so that the total volume flow, which is composed of the sum of the exhaust gas volume flow and the dilution air volume flow, remains constant. The dilution of the exhaust must be high enough so as to prevent the condensation of water from the exhaust both in the dilution tunnel and during the sampling, whereby a maximum temperature at the particle filter may not be exceeded during the particle emission measurement.

The applicable CVS condition in the system is as follows:
Exhaust volume flow x dilution ratio=constant
or
Exhaust volume flow+dilution air volume flow=constant
The dilution ratio DR is defined as:
DR=(dilution air flow+exhaust volume flow)/exhaust volume flow The CVS condition results in a high dilution ratio for operating points with a low exhaust volume flow and a low dilution ratio for operating points with a high exhaust volume flow.

The advantage of the CVS principle consists primarily in the fact that, although the volume flow of the exhaust from an internal combustion engine is variable, the total volume flow consisting of the exhaust and air is held constant—thereby allowing the determination of the particulate emissions or the concentration of gaseous pollutants in a simple manner. There is no need to go into the details of the determination, which is well known to a technician skilled in the art and also described in the above referenced EU Directives and US Regulations.

Figure 1:
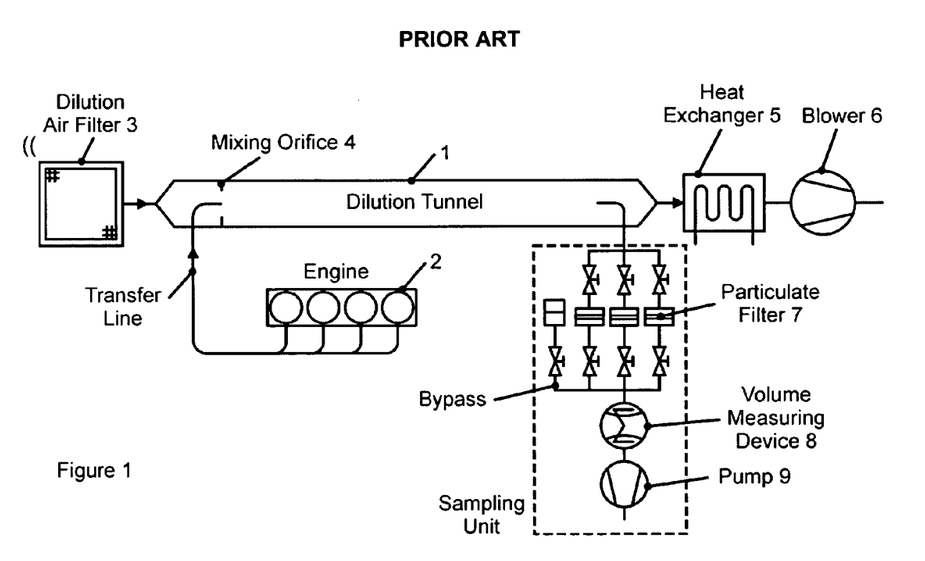
FIG. 1 is a schematic diagram of a conventional CVS device.

A conventional CVS system as illustrated in FIG. 1 for a diesel engine 2, for example, consists of the following individual components: dilution air filter 3, dilution tunnel 1, sampling unit and suction or intake unit in form of a blower 6. The mixing of ambient air and exhaust takes place in the dilution tunnel 1, where a mixing orifice 4 is commonly used to promote a thorough mixing. At the end of the tunnel is the suction unit, which consists either of a positive displacement pump or the blower 6, which delivers a constant volume flow, or which consists of a blower, for example, which can optionally be downstream from one or more venturis. Independently of the blower, a heat exchanger 5 is located upstream from the suction unit to ensure the constancy of the volume flow and to protect the blower or pump, respectively.

The sampling unit is used to collect the particulates on a filter 7. For that purpose, a defined partial sampling flow of the diluted exhaust is extracted or drawn from the dilution tunnel 1 by means of a sampling probe with the assistance of the sampling pump 9. During a particulate emissions measurement, the partial sampling flow is passed through a filter holder containing primary and secondary particulate filters 7, and is recorded by means of a suitable instrument for the measurement of volume and mass, respectively. The partial sampling flow is drawn by a pump through a volume measuring device 8 that is located upstream from the filter. For the measurement of the gaseous components, which is not illustrated here, the partial sampling flow is pumped into bags.

Various solutions have been proposed in terms of measurement equipment for the purpose of measuring the lower emissions levels of engines. However, quite a few of the solutions are based on systems that use a dilution of a small fraction of the total flow, such as the methods disclosed in DE 41 21 928 A1 and U.S. Pat. No. 6,112,575, for example. In these methods of the prior art, the exhaust volume flow is precisely measured continuously, and an attempt is made to adjust the dilution of the partial sampling flow so as to achieve a better measurement accuracy. In the Bag Mini Diluter (BMD) promoted by the United States Environmental Protection Agency (EPA), the current exhaust volume flow must be known at every point during the test cycle. In this system, the dilution ratio is kept constant at every point during the test cycle, so that the diluted fraction or portion of the exhaust volume flow must be adjusted sufficiently dynamically to guarantee the constancy required for accurate measurement results.

Periodically measuring the exhaust volume flow, for example, for every second during the test with such partial sampling or partial flow dilution systems is problematic, because the exhaust volume flow generally can only imprecisely be measured, whereas such measurement is absolutely essential for an evaluation of the pollutant emissions in the systems described in the preceding section. These drawbacks also hold true for the partial flow dilution system of WO 9601998 A in which an exactly constant dilution ration is provided by proportional control of a non-diluted partial exhaust gas flow and a dilution gas both being regulated by pressure control means. The exhaust gas is measured per second in a measuring tube. For allowing extraction of the non-diluted partial exhaust flow in the measuring tube, an element for achieving a calm flow is provided which element eliminates pressure pulsations. Otherwise, the desired small exhaust gas partial amounts of, for example, only 1 percent of the undiluted exhaust volume flow could not be reliably extracted.

One advantage of the CVS systems, on the other hand, is that it is not necessary to determine the exhaust volume flow during the test. As described above, in the CVS systems the dilution ratio in the dilution tunnel changes constantly, because the exhaust volume flow varies continuously during a test cycle, although the total volume flow remains constant. Because the dilution ratio must be adjusted for the highest exhaust volume flow that occurs during the test cycle such that condensation of water is prevented, the dilution ratios are principally high for lower exhaust volume flows. Furthermore, because a constant partial sampling flow of the diluted exhaust is extracted, there are very low pollutant concentrations available for the measurement performed using the particulates filter or the collecting bag.

U.S. Pat. No. 6,405,577 describes a full-flow dilution CVS system in which this problem is discussed in regard to the determination of gaseous pollutant concentrations. Variable venturis are used to vary both the total volume flow as well as the partial sampling flow diverted from the total flow, as a function of the operating conditions of the vehicle being tested. For that purpose, a control unit is used that takes into consideration the different operating conditions during the test cycle, as well as, optionally, information on the current operating conditions supplied directly from the vehicle control system. The operating conditions are thereby divided into phases, whereby in each phase a suitable constant total volume flow is set by means of the variable venturi. The partial volume flow is correspondingly adjusted so that a constant ratio between partial flow and total volume flow results.

The total volume flow is determined by means of a detector mechanism combined with the variable venturi. The current flow rate of the total volume flow is calculated on the basis of the pressure and the temperature at the input of the total volume flow venturi, and with reference to the current setting of the variable venturi. For this purpose, there are provided pressure and temperature sensors in the above-mentioned detector mechanism.

In addition, in order to accurately determine the concentrations of gaseous pollutants, the flow rate of the exhaust is calculated by subtracting the current flow rate of the fresh air fed into the system from the instantaneous flow rate in the total volume flow. The venturi is controlled as a function of the specified operating conditions in several pre-defined stages; and the total volume flow produced is continuously calculated from the venturi settings and detected temperature and pressure values, and is used to adjust the partial sampling flow.

The stages or levels in which the total volume flow is kept at a constant value according to the CVS method are adjusted so that the exhaust volume flow does not exceed the total volume flow at any point. As a rule, therefore, the dilution ratio in the individual stages is not identical. In other words, in this system a test cycle is divided into sub-cycles of different volume flow levels each fulfilling CVS requirements, whereby the sub-cycles are adjusted as a function of the operating conditions.

SUMMARY OF THE INVENTION

An object of the invention is to provide a method and a device to measure the exhaust gas from internal combustion engines (gasoline engines and diesel engines) using a full-flow dilution method, which device and method are suitable for measurement of particulates as well as for a measurement of the concentration of gaseous emission components, and which method and device require little technical effort or expense to handle low pollutant concentrations. This object can be accomplished by the subject matter disclosed in the independent claims. Preferred developments of the invention are disclosed in the dependent claims.

The invention teaches that, in contrast to the conventional CVS system of the prior art, the total volume flow is not kept constant. Nor is there any subdivision of the respective measurement cycle into CVS phases with different levels. Instead, the total volume flow is tracked or proportionally controlled to follow a smoothed curve of the exhaust flow. The term "exhaust flow" is used herein to mean the exhaust volume flow and/or the exhaust mass flow. Optionally, either or both exhaust flows can be measured, and a measured exhaust mass flow can be converted into the exhaust volume flow using the ideal gas equation. Finally, it is also possible, if desired, to replace the tracking or proportional control of the exhaust volume flow by a tracking or proportional control of the exhaust mass flow. The curve of the total volume flow (total mass flow) therefore follows or tracks the curve of the smoothed exhaust flow (exhaust volume flow or exhaust mass flow) as a function of time, and specifically with the ordinate values shifted by the amount of a selected constant dilution ratio. In other words, the proportionality factor of the adjustment for a measurement cycle is predetermined by the desired dilution ratio.

For the purpose of proportional control as claimed herein, the delivery or displacement power of a device used for drawing the total volume flow is preferably adjusted correspondingly. A technically simple and therefore preferred solution is to use and adjust the rotary speed of a positive displacement pump, for example a rotary piston blower. Preferably, a Roots blower is used. As a result of this continuous proportional control, the dilution ratio is kept relatively constant, namely with regard to the smoothed curve of the exhaust gas flow. One disadvantage that might be seen when compared with the system described in U.S. Pat. No. 6,405,577 is the fact that the present invention requires a measurement of the exhaust flow, to be able to determine the averaged or smoothed curve of the exhaust flow. However, the present invention does not require measuring the exhaust volume flow or the exhaust mass flow accurately, which means that this measurement can be performed at low extra cost and effort. Finally it is possible to perform such measurement preferably before the actual test cycle, as explained in greater detail below, so that the exhaust flow no longer needs to be measured during the test cycle itself.

For the determination of the exhaust volume curve, which can alternatively also be done in such a measurement cycle that precedes the actual test cycle, the exhaust volume flow can be measured continuously from the total volume flow and the air volume flow drawn in, while the total volume flow is kept constant. For this purpose, for example, a device of the type used in conventional CVS systems to measure the air that is drawn into the dilution tunnel, can be utilized. One requirement for this type of determination of the exhaust volume flow curve is that the value of the total volume flow must be set sufficiently high that the dilution ratio being now variable does not become too low. During the actual test cycle, the smoothed exhaust flow curve of such a measurement cycle can then be used for the proportional control of the total volume flow according to the invention at a constant dilution ratio with regard to the smoothed exhaust flow curve.

If the dilution ratio in the method taught by the invention is selected so that it is as low as possible and just as low to prevent the condensation of water and to keep the filter temperature from exceeding 51.7° C. or 3% CO2 in the collection bag, a higher concentration of gaseous pollutants in the diluted exhaust or a higher charge on the particle filter can be ensured—thus ensuring a better measurement accuracy than when the total volume flow is kept constant. In terms of practical implementation, that means that the optimum dilution ratio for the respective engine is determined, and then, using that ratio as a factor for the proportional control, the total volume flow can be adjusted to follow the smoothed curve of the exhaust flow.

In the present invention, the reference value for the measurement is not the exhaust volume flow of the engine, but the total volume flow consisting of the exhaust and the dilution air. The partial flow of the diluted exhaust for sampling passing through a particle filter or into the collecting bag is preferably adjusted in relation to the total volume flow so that a constant ratio of these two values is maintained during the test cycle.

The requirement can be stated as follows: partial sampling volume flow/total volume flow=constant. This ratio, which is kept constant for a measurement cycle, can, for example, be adapted for high and low concentrations of pollutants, to further optimize the accuracy of the measurement. For a low concentration of pollutants, for example, the ratio will therefore be set higher.

Although it is not in compliance with current legal provisions, it would also be possible to have defined variations of the ratio between the total volume flow and the partial sampling volume flow within the measurement cycle, and to take them into consideration when determining the emission values. In the currently specified formula for the measurement of particulate emissions, it would already be possible to take such a defined variation in the partial sampling volume flow into consideration.

Because the total volume flow is adjusted proportional to a smoothed curve of the exhaust volume flow, the partial volume sampling flow from the diluted exhaust has to be regulated only slowly. The problems of a dynamic measurement of the partial sampling volume flow or total volume flow disappear. The total volume flow, for example, can easily be determined from the rotational speed of a suction device and its volume.

To be able to freely select the rotational speed and thus the delivery of the suction or exhaust device, and to be able to vary it continuously within the dynamic limits of the suction device, preference is given to the use of a Roots blower which is driven by an electric motor, which is in turn controlled by a frequency inverter. This arrangement represents an economical and technically simple solution. Theoretically it is possible to use any type of suction device for the total volume flow, with which the total volume flow can be regulated so that it corresponds to the smoothed curve of the exhaust volume flow. Because the extraction or suction device for the partial sampling volume flow also does not have to exhibit a fast dynamic response, but can slowly be readjusted, this adjustment can also be made with little technical effort or expense. In concrete implementations to measure gaseous emissions, membrane vacuum pumps were used to achieve the required gas tightness, while vane-type rotary pumps preceded by a mass flow controller were used to measure particulate emissions. Alternatively, the pumps can be adjusted without a mass flow controller. Finally, although it is not preferred according to the invention, venturis in combination with positive displacement pumps or blowers can be used both for the total flow and for the partial sampling flow, in order to control the two variables proportionally.

The requirements for the dynamic response of the control system can be selected nearly without restriction. The dynamic response of the extraction or drawing device for the partial sampling flow, and that of the blower for the total volume flow, have to be taken into consideration. The gradient of the smoothed curve of the exhaust volume flow must not exceed a maximum value which depends on the respective system and which can still be afforded by the system's dynamic response. Depending on the implementation of the suction devices for the partial sampling and total volume flows and their dynamic response, one will take into consideration the device with the poorer dynamic response when specifying the smoothing algorithm in such a manner that the desired curve can also be followed by this device.

The invention will normally be applied to non-steady-state test cycles with varying engine loads. Theoretically, however, the method claimed by the invention can also be applied to tests with steady-state operating points.

BRIEF SUMMARY OF THE DRAWINGS

The invention is explained in greater detail below with reference to the accompanying drawings, in which.

DETAILED DESCRIPTION OF THE PREFERRED EMBODIMENTS

Figure 2A:
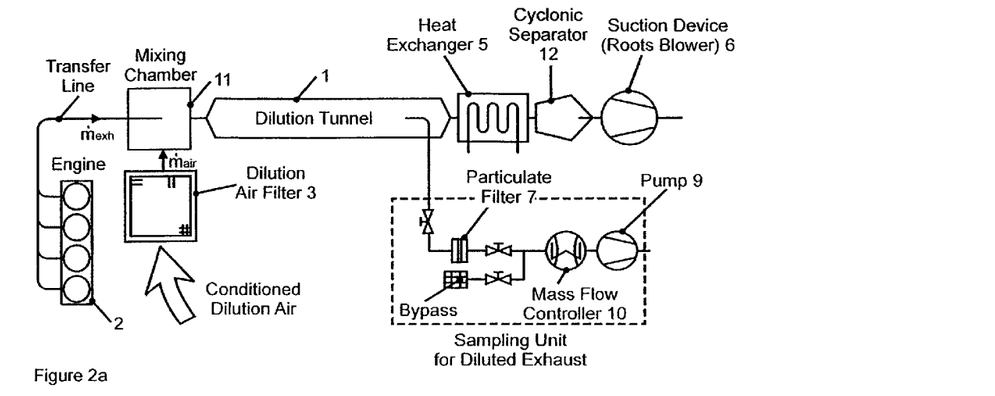
FIGS. 2a and 2b are schematic diagrams of an exemplary embodiment of a device incorporating the present invention for emission measurement of particulate and gas components.

As illustrated in FIG. 2a, the exhaust from a diesel engine 2 is first conducted to a mixing chamber 11 in which it is mixed with filtered dilution air, and is then conducted to a dilution tunnel 1. At the end of the dilution tunnel, a partial sampling volume flow of the diluted exhaust-air mixture is extracted into a sampling unit and is drawn through a filter holder by means of a vane-type rotary pump 9. The filter holder can hold Teflon-coated fiberglass filters 7, for example. A mass flow controller 10 proportionally controls the partial sampling volume flow. The particulate charge of the filter 7 is measured by means of a pressure sensor (not shown).

Downstream from the dilution tunnel 1 and the extraction point for the partial sampling volume flow, the diluted exhaust-air mixture passes through a heat exchanger 5 which cools it to a defined temperature, for example to approximately 25 C., before it travels through a cyclone 12 to a Roots blower 6. The purpose of the cyclone 12 is to remove the particulates from the exhaust-air mixture before they reach the Roots blower 6. The Roots blower 6 is thereby effectively protected against soot deposition.

In systems with venturis as suction and extraction devices for the total and partial sampling volume flow requiring an accurate measurement of pressure and temperature, the sample extraction point for measurement of gaseous emissions is generally downstream from the heat exchanger. Vis-a-vis such systems, a fundamental advantage in the inventional use of a blower with controllable rotational speed is that the speed control thereof does not require accurate measurement of pressure or temperature.

The Roots blower 6' is operated by an electric motor (not shown), and the speed of the blower can be varied by means of a frequency inverter (not shown) at the electric motor. The invention teaches that, during a test cycle, different total volume flows for the diluted exhaust can thus be realized, and thus relatively constant dilution ratios can be adjusted and maintained. The extraction device for the extraction of the partial sampling flow is regulated or controlled in proportion to the variations in the total volume flow. The emissions are determined, according to the specifications set by the applicable laws, from the total volumes and partial sampling flow volumes of the diluted exhaust integrated over the length of a test cycle.

The following components were used in a device employed in actual practice: the Roots blower was a Delta Blower G M 15L manufactured by Aerzener Maschinenfabrik with speeds of up to 4800 rpm, the electric motor to operate the blower was a 4 kW three-phase squirrel-cage motor manufactured by ABB Motors Oi, the frequency inverter was Model ACS 601 manufactured by ABB Motors Oi, a vane-type rotary vacuum pump Model VCE 40 manufactured by Rietschle was used as the extraction pump for the partial sampling flow in FIG. 2a together with a mass flow regulator in form of a gas flow controller Model 1559 manufactured by NKS Instruments. Except for a dilution air filter manufactured by Pierburg GmbH, the rest of the components such as the heat exchanger, dilution tunnel, mixing chamber and cyclone were designed by the Technical University of Darmstadt.

Figure 2B:
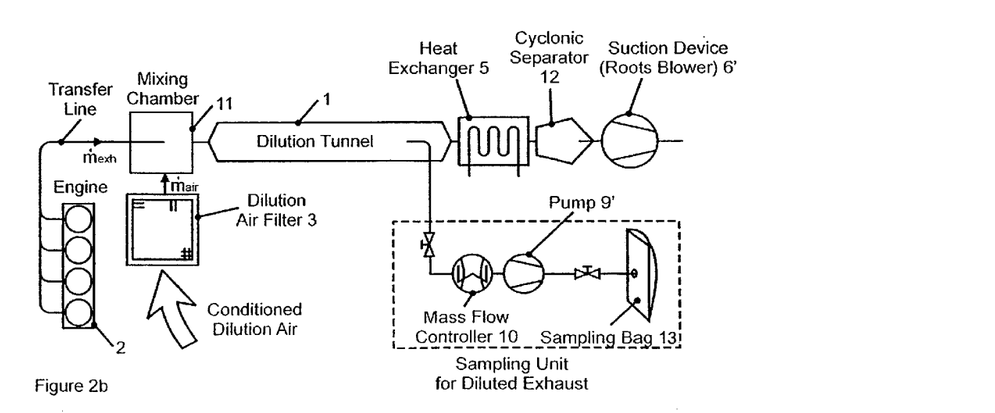

FIG. 2b shows a possible device in accordance with the present invention to measure the emission of gaseous components by means of a sampling bag 13. In this case, for example, a membrane pump 9' (for example Vaccubrand GmbH dual head membrane pump) is used due to the required air tightness. The pump 9' and the mass flow regulator 10 are located upstream from the sampling bag 13. There are a number of other possible designs that can be used for the sampling unit. In accordance with the present invention, it is only necessary to ensure that the partial sampling flow extracted can be proportionally controlled as required.

One preferred possibility of determining the smoothed flow of the exhaust volume flow is to first record the exhaust volume flow, e.g. per second, in the respective test cycle on a test engine or a test vehicle. Based on the principle taught by the invention, an exact measurement of the exhaust volume flow is not necessary. For example, the exhaust mass flows can be determined by a one-second measurement of the fuel mass by means of a fuel scale and a measurement of the mass of air drawn in at the inlet of the engine, and the exhaust volume flow curve can then be calculated from those values by means of the ideal gas equation. For this purpose, the fuel mass flow and the air mass flow are added and any differences in the cycle time or measurement time are corrected. Alternatively, one can also use a measurement instrument in the exhaust line, for example, which uses an ultrasound measurement, a pressure measurement or another method.

With a one-second measurement of the exhaust volume flow, for example, a sliding average over 10 individual measurements is reasonable, whereby a subsequent filtering with an FFT (Fast Fourier Transform) filter can be used to remove any remaining rapid fluctuations from the smoothed curve. If the measurements are recorded with a greater or lesser frequency, the selected window for the sliding average can be narrower or wider. Sliding averaging with subsequent filtering in an FFT filter, or also in a Butterworth filter, for example, constitutes a precise method of obtaining the averaged curve of the measured values. Alternatively, a filter with a calibrated smoothing algorithm can also be used. Finally, it is also possible to smooth the measured curve by means of an integrating measurement during the actual measurement. In that case, however, an offset is unavoidable which varies depending on the measurement environment, so that the mathematical and technical effort required are comparatively high.

A preferred embodiment of the invention consists in recording and smoothing the entire curve of the exhaust gas in a preliminary test cycle preceding the actual test cycle for determining the emissions values. Then the recorded smoothed curve is used in the subsequent measurement cycle for the proportional control of the total volume flow. This method has been found to work successfully. Of course, the exhaust volume flow can also be measured and smoothed during this emission measurement cycle, and the smoothed curve determined previously can be corrected if necessary. In the tests performed so far, however, this measure has not been necessary, and it has been sufficient for an emission test cycle to previously record the exhaust volume flow only once and to have its smoothed curve available for the subsequent emission measurement(s).

The smoothed curve need not by any means be a precise reproduction of the exhaust volume flow. Short minor peaks in the actual exhaust volume flow above the smoothed curve do not necessarily result in the condensation of the water in the diluted exhaust. Depending on the tendency of an individual engine to produce combustion water, a safety margin that is adapted to the degree of this tendency will be provided by the dilution ratio which is adjusted to a sufficiently high value.

Figure 3:
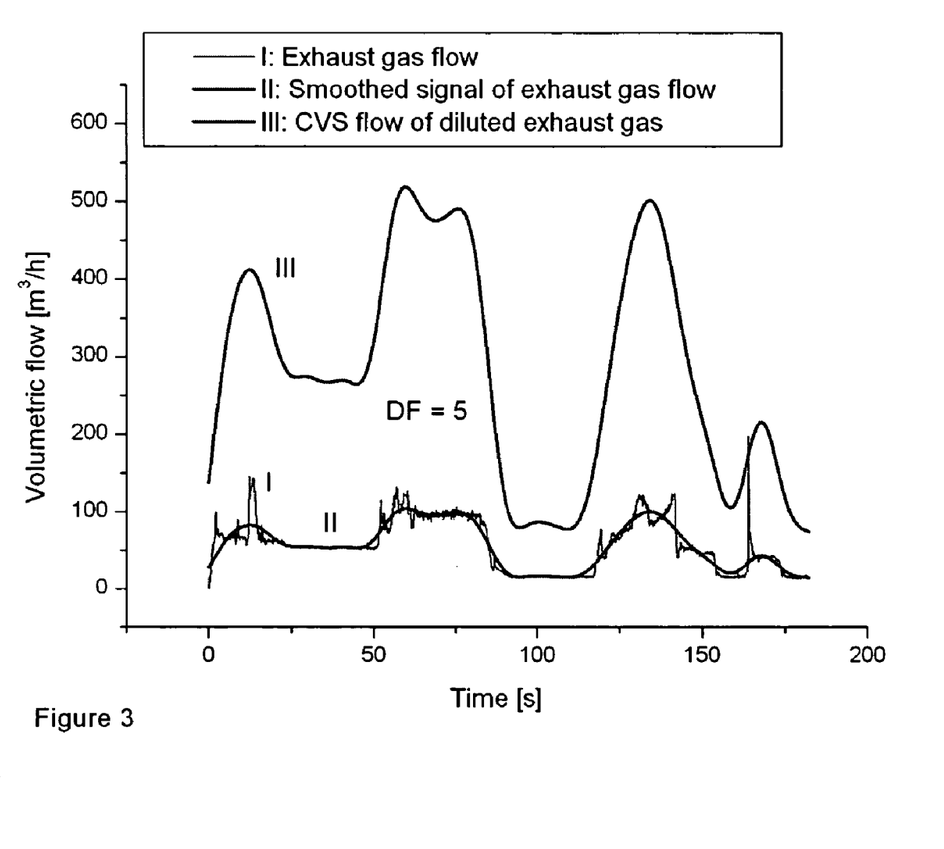
FIG. 3 is the curve of an example for smoothing an exhaust volume flow and the corresponding control of the total volume flow.

To realize the proportional tracking control of the total volume flow, a rotational speed control device for the Roots blower was operated as described below. The exhaust volume flow I was calculated from the exhaust mass flow curve that was plotted with the values for air and fuel mass flows. A sliding average was calculated for 10-second periods and an FFT filtering performed for 100 values. The result II of this smoothing of the exhaust flow I is illustrated in FIG. 3. The proportional total volume flow curve III with a dilution ratio of 5 is also shown in FIG. 3. For this curve, the corresponding required rotational speed values were determined and the current of the electric motor of the Roots blower was adjusted accordingly by means of the frequency inverter. In an implementation, smoothing was provided using the software Origin of Originlabs, version 6.1G. The program effects a low pass filtering of 0.01 Hz in a first step and smoothing over 100 points as outlined above in a second step of the smoothing program.

For the measurement of particulates as well as for the measurement of gaseous components in the emissions, the values determined in accordance with the inventional method were compared with the values determined using a conventional device as illustrated in FIG. 1. The method claimed by the invention achieved a comparatively higher measurement accuracy.

As already outlined above, obtaining the desired emission values from the measured sample unit values has to follow the strict EU or US regulations, respectively. Nevertheless, the relevant formulas and essential features for calculation and measurement are given below.

In case of gaseous emissions, a proportional partial sampling flow is drawn from the diluted exhaust as indicated in FIG. 2b in order to fill the collecting bags. Depending on the emission value of the respective engine to be tested, approximately 0.1 to 0.15% of the rate of flow of the diluted exhaust gas are drawn. During test cycle, the partial sampling flow is supplied to different bags according to the respective actual test phase. At the end of the test cycle, the content of the bags is determined regarding $NO_x$, CO, HC und $CO_2$.

In case of measurement of particulate emissions (FIG. 2a) the partial sampling flow drawn is again proportionally controlled with regard to the total flow rate through the tunnel. In this case, a varying pressure drop due to the varying partial sampling flow may have to be taken into consideration when determining the weight increase of the respective filter. However, this could successfully be handled. For this purpose, the actual partial sampling flow was continuously compared to the desired value of the partial sampling flow in order to detect a decrease of the partial sampling flow due to too high pressure drops. For particulate emissions, 0.4 to 0.5% of the tunnel flow rate were drawn as partial sampling flow. The weight of the particle filters before and after the respective tests was determined in accordance with said regulations.

1 The emission values can be determined as follows:

1.1 Determination of Volume

The volume of the diluted exhaust gas as measured by the positive-displacement pump in form of a Roots blower used in the present invention is determined by the following formula:

$$V = V_0 \cdot N,$$

wherein

V: is the uncorrected volume of the diluted exhaust gas in $m^3$/test, $V_0$: is the gas volume drawn by the pump under test conditions in 1/rotation N: number of rotations of the pump during test The Roots blower is calibrated in accordance with the regulations for a plurality of rotational speeds and, hence, flow rate regions. A characteristic map representing the relationship between flow rate and rotational speed is then established.

The volume of the diluted exhaust gas is corrected by the following formula to standard temperature/pressure conditions:

$$V_{mix} = V \cdot K_i \cdot \frac{P_B - P_i}{T_P},$$

wherein:

$$K_i = \frac{273{,}2 \text{ K}}{101{,}33 \text{ kPa}} = 2{,}6961 \ (K \cdot kPa^{-1})$$

$P_B$: air pressure in the test environment in kPa, $P_i$: pressure difference between the reduced pressure at the inlet of the positive-displacement pump and the environmental pressure in kPa, $T_P$: medium temperature in K of the diluted exhaust gas at the entrance into the positive-displacement pump during test condition.

1.2 Determination of Gaseous Emissions

The amounts of gaseous emissions are determined in accordance with the following formula:

$$M_i = \frac{V_{mix} \cdot Q_i \cdot k_H \cdot C_i \cdot 10^{-6}}{d},$$

wherein:

$M_i$: emitted gaseous pollutants i in g/km or g/mile, $V_{mix}$: volume of diluted exhaust gas in 1/test and corrected to standard conditions (273,2 K; 101,33 kPa), $Q_i$: density of the pollutant i in g/l at standard temperature and pressure (273,2 K; 101,33 kPa), $k_H$: humidity correction factor for calculating emitted nitrogen oxide amounts (for HC und CO there is no humidity corrections), $C_i$: concentration of pollutant i in the diluted exhaust gas in ppm and corrected by the pollutant concentration i in dilution air, d: distance corresponding to the driving cycle.

The concentration of pollutants in the collecting bag is then corrected by the concentration in a collecting bag for dilution air:

$$C_i = C_e - C_d \cdot \left(1 - \frac{1}{DF}\right),$$

wherein:

$C_i$: concentration of the pollutant i in the diluted exhaust gas in ppm and corrected by the concentration of the pollutant i in the dilution air, $C_e$: measured concentration of the pollutant i in the diluted exhaust gas in ppm, $C_d$: measured concentration of the pollutant i in the air used for dilution in ppm, DF: dilution factor:

$$DF = \frac{13{,}4}{C_{CO2} + (C_{HC} + C_{CO}) \cdot 10^{-4}},$$

wherein:

$C_{CO2}$: $CO_2$-concentration in the diluted exhaust gas in the collecting bag in % by volume $C_{HC}$: HC-concentration in the diluted exhaust gas in the collecting bag in ppm carbon equivalent, $C_{CO}$: CO-concentration in the diluted exhaust gas in the collecting bag.

The humidity correction factor for NO is calculated as outlined in the regulations (Official Journal No. L242 of Aug. 30, 1991, page 79).

Knowledge of the partial volume drawn for the bag filling is not necessary.

1.3 Determination of Particle Emission

The particle emission value $M_p$ (g/km for EU or g/mile for US) is calculated in accordance with the following formula:

$$M_p = \frac{(V_{mix} + V_{ep}) \cdot P_e}{V_{ep} \cdot d},$$

wherein:

$V_{mix}$: volume of the diluted exhaust gas under standard conditions, $V_{ep}$: volume of the exhaust gas flown through the particle filter under standard conditions, $P_e$: mass of the particles deposited on the filter, d: distance corresponding to the driving cycle in km or mile, $M_p$: particle emission in g/km or g/mile 2 Example for Calculation of Emission Environmental Conditions:

environmental temperature: 25° C.=297,2 K air pressure: $P_B$=100,2 kPa

Relative humidity: $R_a$=45%

Saturation vapor pressure for water at 25° C.: $P_d$=3,17 kP

Volume of the total flow of diluted exhaust gas through the a full flow dilution system measured and corrected to standard conditions of temperature and pressure during the test cycle : V=63,24 $m^3$ Measured values of concentration for respective collecting bags:

| | Sample with diluted exhaust gas | Sample with dilution air |
|---|---|---|
| HC | 19.2 ppm | 0.9 ppm |
| CO | 18.3 ppm | 1.1 ppm |
| $NO_x$ | 47 ppm | 0.1 ppm |
| $CO_2$ | 2.4 Vol % | 0.04 Vol % |

The humidity correction factor for $NO_x$ and the dilution factor DF are calculated:

$k_H$=0,946

DF=5,57

Thereafter, the corrected pollution concentrations in the collecting bag are calculated:

HC, Mass of the Emissions:

$C_i$=19,2−0,9*(1−⅕,57)=18,5

$$M_{HC} = C_{HC} \cdot V_{mix} \cdot Q_{HC} \cdot \frac{1}{d}$$

$Q_{HC}$=0,619

$M_{HC}$=0,723/d g/km

CO, Mass of the Emissions:

$C_i$=18,3−1,1*(1−⅕,57)=17,4

$$M_{CO} = C_{CO} \cdot V_{mix} \cdot Q_{CO} \cdot \frac{1}{d}$$

$Q_{CO}$=1,16

$M_{CO}$=1,28/d g/km $NO_x$, Mass of the Emissions:

$C_i$=47−0,1*(1−⅕,57)=4,4

$$M_{NOx} = C_{NOx} \cdot V_{mix} \cdot Q_{NOx} \cdot k_H \cdot \frac{1}{d}$$

$Q_{NOx}$=1,91

$M_{NOx}$=5,37/d g/km $CO_2$, Mass of the Emissions:

$C_i$=47−0,1*(1−⅕,57)=4,4

$$M_{CO2} = C_{CO2} \cdot V_{mix} \cdot Q_{CO2} \cdot \frac{1}{d}$$

$Q_{CO2}$=1,83

$M_{CO2}$=2739,5/d g/km

For calculating the particle emission the weight of the filters before and after the particle emission is determined.

The partial volume drawn over the filters is integrated by the computer during the test cycle:

$$V_{ep}=590{,}79$$

$$P_e=3{,}108$$

$$M_p=0{,}34$$

General Note: The above determinations have been made for a specific diesel engine. In case of HC, the emission has to be determined exclusively with heated FID online from the dilution tunnel. This signal is integrated and replaces $C_{HC}$ in each one of the relevant formulas.

The invention claimed is:

1. A method for measurement of exhaust gas from internal combustion engines using a full-flow dilution method and subjecting an internal combustion to at least one of a plurality of specified test cycles, comprising:
varying an exhaust flow of the internal combustion engine during said at least one test cycle;
mixing the exhaust flow of said internal combustion with dilution air so that, in said at least one test cycle, a defined total flow results;
extracting a partial sampling flow from said total flow during said test cycle, said partial sampling flow being used for measuring emission values of the exhaust gas, wherein a smoothed curve of the varied exhaust flow is determined such that the gradients of the smoothing applied during formation of the smoothed curve of the exhaust flow are limited to maximum values and wherein said maximum values are determined from possible gradients in the control dynamic which can be afforded by devices used for drawing the total flow and partial sampling flow, respectively, and the total flow is subjected to a proportional control in respect of variations in the obtained smoothed curve of the exhaust flow.

2. Method as recited in claim 1 wherein the emission values are the values of particulate emissions or gaseous components or of both.

3. Method as recited in claim 1 wherein said proportional control is accomplished by controlling a rotary piston blower being used for drawing the total flow.

4. Method as recited in claim 3 wherein a Roots blower is used as said rotary piston blower.

5. Method as recited in claim 1 wherein said extracted partial sampling flow is adjusted in relation to the total flow to achieve a constant ratio of the partial sampling flow to the total flow.

6. Method as recited in claim 1 wherein the smoothed curve of the exhaust flow is determined in a preliminary cycle that precedes the actual test cycle for the emissions measurement, and the curve obtained in said preliminary cycle is utilized for the proportional control during the actual test cycle.

7. Method as recited in claim 1 wherein a fuel mass and an air mass at the engine inlet are measured in order to determine the smoothed curve of the exhaust flow.

8. Method as recited in claim 1 wherein, for determining the smoothed curve of the exhaust flow, exhaust flow values of the respective test cycle are determined and are subjected to one of the following steps: sliding averaging and filtering, filtering with simultaneous smoothing.

9. A device for measurement of exhaust gas from internal combustion using a full-flow dilution method and subjecting an internal combustion engine to at least one of a plurality of specified test cycles, comprising:
means for varying an exhaust flow of the internal combustion engine during said at least one test cycle;
mixing means for mixing the exhaust flow of said internal combustion machine with dilution air so that in said at least one specified test cycle, a defined total flow results;
pump means for extracting a partial sampling flow from said total flow during said test cycle, said partial sampling flow being used for measuring emission values of the exhaust gas;
means for determining a smoothed curve of the varied exhaust flow, wherein the smoothed curve is determined such that the gradients of the smoothing applied during formation of the smoothed curve of the exhaust flow are limited to maximum values and wherein said maximum values are determined from possible gradients in the control dynamic which can be afforded by devices used for drawing the total flow and partial sampling flow, respectively; and
control means for subjecting the total flow to a proportional control in respect of variations in the obtained smoothed curve of the exhaust flow.

10. Device as recited in claim 9 wherein the emission values are the values of particulate emissions or gaseous components or of both.

11. Device as recited in claim 9 wherein said proportional control is accomplished by regulating a rotary piston blower being used for drawing the total flow.

12. Device as recited in claim 11 wherein said rotary piston blower is a Roots blower.

13. Device as recited in claim 9 wherein said means for extracting comprise control means for adjusting the partial sampling flow in relation to the total flow to achieve a constant ratio of the partial sampling flow to the total flow.

14. Device as recited in claim 9 wherein said determining means determine the smoothed curve of the exhaust flow in a preliminary cycle that precedes the actual test cycle for the emissions measurement, and utilizes the curve obtained in said preliminary cycle for the proportional control during the actual test cycle.

15. Device as recited in claim 9 wherein said determining means comprises measuring means for measuring a fuel mass and an air mass at the engine inlet in order to determine the smoothed curve of the exhaust flow.

16. Device as recited in claim 9 wherein said determining means determines the exhaust flow values of the respective test cycle and subjects the measured values to one of the following steps: sliding averaging and filtering, filtering with simultaneous smoothing.

* * * * *